United States Patent [19]
Wanner

[11] Patent Number: 5,580,793
[45] Date of Patent: Dec. 3, 1996

[54] PROCESS AND DEVICE FOR DETERMINING THE PARA CONTENT OF A HYDROGEN GAS STREAM

[75] Inventor: Manfred Wanner, München, Germany

[73] Assignee: Linde Aktiengesellschaft, Wiesbaden, Germany

[21] Appl. No.: 382,789

[22] Filed: Feb. 2, 1995

[30] Foreign Application Priority Data

Feb. 3, 1994 [DE] Germany ............ 44 03 352.4

[51] Int. Cl.⁶ .................................................. G01N 25/20
[52] U.S. Cl. .................. 436/144; 422/62; 422/80; 422/83; 436/50; 436/147; 436/148; 73/25.01; 73/25.05; 423/648.1; 423/649
[58] Field of Search ................ 422/62, 80, 83; 436/50, 144, 147, 148; 73/25.01, 25.05; 423/648.1, 649

[56] References Cited

U.S. PATENT DOCUMENTS

| | | | |
|---|---|---|---|
| 2,234,128 | 3/1941 | Miller | 73/25.01 |
| 2,937,076 | 5/1960 | Class et al. | 23/210 |
| 2,943,917 | 7/1960 | Weitzel | 423/649 |
| 3,043,110 | 7/1962 | Ahern | 423/649 |
| 3,092,461 | 6/1963 | Arend et al. | 423/649 |
| 3,094,390 | 6/1963 | Vander Arend | 423/649 |
| 3,095,274 | 6/1963 | Crawford | 423/649 |
| 3,116,115 | 12/1963 | Kasparian et al. | 423/649 |
| 3,180,709 | 4/1965 | Yendall et al. | 423/649 |
| 3,375,076 | 3/1968 | Vander Arend | 423/649 |
| 3,380,809 | 4/1968 | Newton | 423/649 |
| 3,383,176 | 5/1968 | Keith | 423/649 |
| 3,535,915 | 10/1970 | Felton et al. | 73/25.01 |
| 3,578,405 | 5/1971 | Woodle | 436/147 |
| 3,725,005 | 4/1973 | Innes | 436/147 |
| 3,992,167 | 11/1976 | Beddome | 62/18 |
| 4,205,056 | 5/1980 | Inokuchi et al. | 423/649 |
| 4,393,039 | 7/1983 | Sherman | 423/648 R |
| 4,474,592 | 10/1984 | Kundig | 62/37 |
| 4,477,413 | 10/1984 | Carson | 422/62 |
| 4,671,080 | 6/1987 | Gross | 62/467 |
| 4,765,813 | 8/1988 | Gaumer, Jr. et al. | 62/20 |
| 5,154,062 | 10/1992 | Gaumer, Jr. et al. | 62/54.1 |
| 5,305,610 | 4/1994 | Bennett et al. | 62/5 |
| 5,374,476 | 12/1994 | Horsley | 428/305.5 |

*Primary Examiner*—Jill Warden
*Assistant Examiner*—Sharidan Carrillo
*Attorney, Agent, or Firm*—Millen, White, Zelane, & Branigan, P.C.

[57] ABSTRACT

Process and device for determining para content $X_1$ of a hydrogen gas stream, in which temperature $T_1$ as well as pressure $p_1$ of the hydrogen gas stream are measured before its entry into at least adiabatically-operated para-ortho-conversion catalyst. The hydrogen gas stream flows through the para-ortho-conversion catalyst until equilibrium is established. Thereafter, temperature $T_2$ as well as pressure $p_2$ of the hydrogen gas stream are measured after the hydrogen gas exits from the para-ortho-conversion catalyst or are measured after the last of the latter exits the catalyst. Para content $X_1$ of the hydrogen gas stream, at the instant before entering the para-ortho-conversion catalyst, is determined by relations $h_1(X_1, T_1, p_1) = h_2(X_2, T_2, p_2)$ and $X_2 = X_g(T_2)$ in equilibrium, in which $h_1$ is the enthalpy of the hydrogen gas stream at the inlet of the para-ortho-conversion catalyst and $h_2$ is the enthalpy of the hydrogen gas stream at the outlet of the para-ortho-conversion catalyst.

13 Claims, 4 Drawing Sheets

PROCESS AND DEVICE FOR DETERMINING THE PARA CONTENT OF A HYDROGEN GAS STREAM

SUMMARY OF THE INVENTION

The invention relates to a process and a device for determining the para content, $X_1$, of a hydrogen gas stream.

Because of its unlimited availability as a component of water, its nonpolluting nature after combustion, its storage capacity and its transportability in the liquid state, hydrogen is among the carriers of energy having a great potential for expanded use in the future.

The hydrogen molecule consists of two hydrogen atoms, which for their part each consist of one proton and one electron each. The hydrogen molecule, $H_2$, exists in two modifications, as orthohydrogen and as parahydrogen, which are distinguished by the spin of their atomic nuclei. In the ortho modification, the two nuclear spins are aligned parallel whereas in the para modification the spins are anti-parallel. The two different orientations of the nuclear spin are responsible for different magnetic, optical and thermal properties of the two modifications.

The equilibrium composition between the ortho and para modification is dependent on temperature and changes from 25% para portion at ambient temperature to 100% para portion at 20K, the boiling point of hydrogen (see FIG. 1). The conversion of ortho- to parahydrogen is exothermic and takes place automatically and slowly, i.e., over several days, but can be accelerated with the help of catalysts, e.g., $Fe_2O_3$, $Ni/SiO_2$, $Ru/Al_2O_3$. Since the heat of transition from ortho to para at the boiling point is about 1.5 times as great as the heat of evaporation, it is inevitable that during prolonged intermediate storage of the hydrogen, in the liquefaction of the hydrogen, the conversion of normal hydrogen to parahydrogen takes place and the heat of transition that is being liberated in this case is dissipated and can lead to evaporation of a portion of the liquefied hydrogen. A purchaser of liquid hydrogen who would like to intermediately store the hydrogen under certain circumstances for several weeks will therefore require of the supplier a para portion of at least 98%. A high para content of the liquid hydrogen minimizes the possibility of the exothermic conversion resulting in evaporation.

Up to now, the determination of the para content of the hydrogen has been based on the principle that ortho- and parahydrogen have slightly different thermal conductivities. By measurement of the thermal conductivity and comparison with a reference gas, the para content of the hydrogen can be determined. However, this measuring technique is comparatively expensive. Thus, because of the increasing number of hydrogen-liquefaction plants to be expected in the near future, a simpler and more inexpensive process for determining the para content of hydrogen is needed.

Therefore, an object of this invention is to provide a simpler and more inexpensive process, in comparison to the prior art, of determining the para content of hydrogen.

Upon further study of the specification and appended claims, further objects and advantages of this invention will become apparent to those skilled in the art.

These objects are achieved according to the invention by a process comprising:

(a) measuring the temperature, $T_1$, as well as the pressure, $p_1$, of a hydrogen gas stream before its entry into the presence of at least one adiabatically-operated para-ortho-conversion catalyst, (b) flowing the hydrogen gas stream through the para-ortho-conversion catalyst until equilibrium is established, (c) measuring the temperature, $T_2$, as well as the pressure, $p_2$, of the hydrogen gas stream after its exit from the para-ortho-conversion catalyst or after the last of the hydrogen gas stream exits the catalyst, and (d) determining the para content, $X_1$, of the hydrogen gas stream at the instant before entering the para-ortho-conversion catalyst by the relationships $h_1(X_1, T_1, p_1) = h_2(X_2, T_2, p_2)$ and $X_2 = X_g(T_2)$ in equilibrium, wherein $h_1$ is the enthalpy of the hydrogen gas stream at the inlet of the para-ortho-conversion catalyst and $h_2$ is the enthalpy of the hydrogen gas stream at the outlet of the para-ortho-conversion catalyst.

Preferably, the catalyst is a metal oxide catalyst, e.g., $Fe_2O_3$, $Ni/SiO_2$ or $Ru/Al_2O_3$, especially iron oxide. The temperature $T_1$ is preferably about 70–140K, especially 105–125K.

The process according to the invention now makes possible in a comparatively simple way the determination of the para content of hydrogen. Also, comparison with a reference gas is unnecessary.

The principle of the process according to the invention is explained in more detail based on FIG. 1 as well as two examples.

BRIEF DESCRIPTION OF THE DRAWINGS

FIG. 4 illustrates a system in accordance with the invention. In the system, a hydrogen liquefier 20 is connected via a line to a hydrogen storage tank 30. A hydrogen gas stream is removed from this connecting line and delivered to a device 10 for measuring para hydrogen content of the hydrogen being transferred from the hydrogen liquefier to the hydrogen storage tank. Device 10 is an apparatus in accordance with the invention for measuring the para hydrogen content of a hydrogen stream such as illustrated in FIGS. 2 and 3.

DETAILED DESCRIPTION

Figure 1:
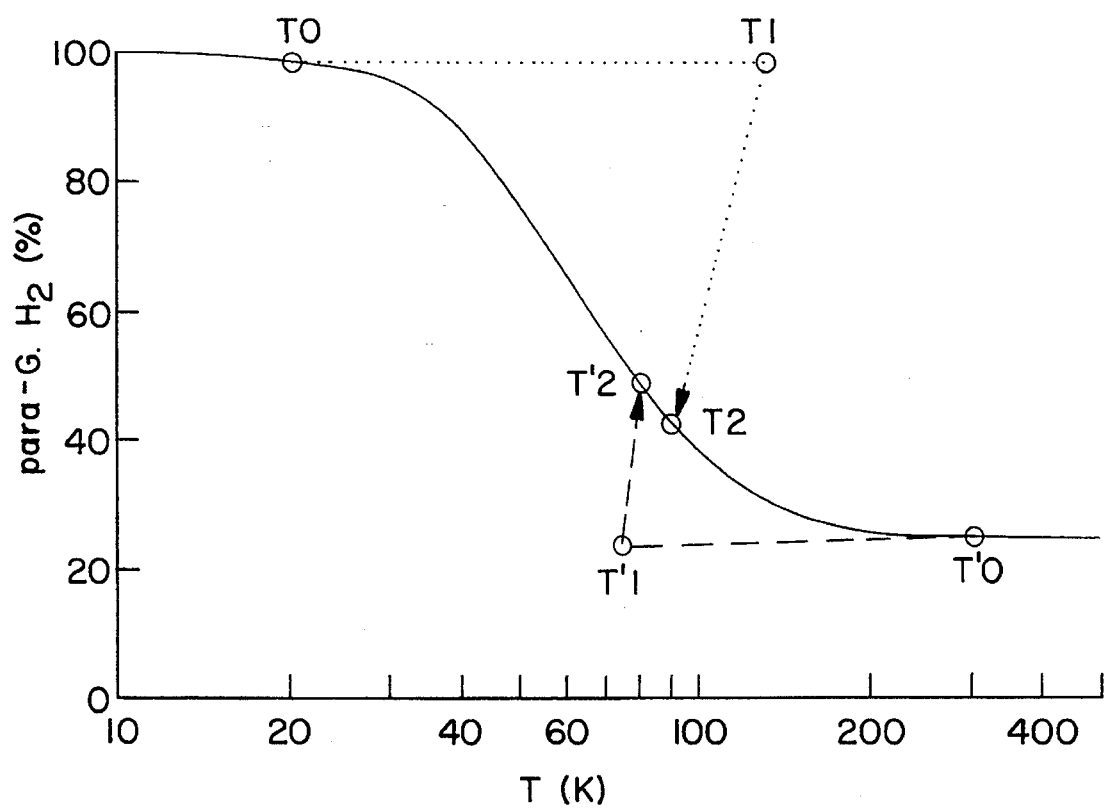
FIG. 1 shows the equilibrium curve (solid line) for the para content of hydrogen as a function of temperature.

The equilibrium curve in FIG. 1 illustrates the dependence of the parahydrogen content of hydrogen on temperature. As already mentioned, the para content of the hydrogen is 25% at ambient temperature and 100% at a temperature of 20K.

EXAMPLE 1

In this example, the hydrogen is, for example, a hydrogen measuring stream removed from the connecting line between a hydrogen liquefier and a hydrogen storage tank. In its removal from the connecting line, the hydrogen measuring stream has temperature $T_0$. During delivery to the measuring device, a heating to temperature $T_1$ takes place. See dotted line in FIG. 1. To prevent a change of the para content occurring as early as during flow through the feed line, corresponding materials, e.g., high-grade steel or copper pipes, are used for the feed line which do not catalyze the conversion from para- to orthohydrogen or vice versa. The hydrogen measuring stream now flows through the para-ortho-conversion catalyst until equilibrium is established, so that it exhibits temperature $T_2$ at the outlet of the para-ortho-conversion catalyst. Corresponding to temperature $T_2$ determined at the outlet of the para-ortho-conversion catalyst, the para content $X_2$ of the hydrogen measuring stream which has flowed through the para-ortho-conversion catalyst can be determined from the equilibrium curve represented in FIG. 1, it being assumed that para content $X_1$ is a clear function of temperature $T_2$. By means of the relation $h_1 (X_1, T_1, p_1) = h_2 (X_2, T_2, p_2)$, the para content $X_1$ of the hydrogen measuring stream can be calculated, e.g., by zero-setting calculation at the instant before entering the para-ortho-conversion catalyst and thus at the time of the removal from the connecting line between hydrogen liquefier and hydrogen storage tank.

The following numerical example is used for further explanation of the process according to the invention:

Measured parameters: $T_1 = 100$ K., $p_1 = 1.2$ bara
$T_2 = 76$ K., $p_2 = 1.2$ bara with $X_2 = X_g (T_2) = 51.5\% \rightarrow h_2 (X_2, T_2, p_2) = -3076.2$ J/g= $h_1 (X_1, T_1, p_1) \rightarrow X_1 = 98\%$ The calculation is facilitated by assuming no appreciable pressure drop, i.e., $p_1 = p_2$. In any event, the sensitivity to pressure drop is negligible.

Regarding enthalpy data for hydrogen, see, e.g., McCarthy, Hydrogen Technical Survey, NASA, SP-3089 (1975).

EXAMPLE 2

In this example, which is illustrated in FIG. 1 by the broken line, a hydrogen measuring stream is present at room temperature ($T'_0$) and thus has a para content of 25%. This hydrogen measuring stream is cooled to temperature $T'_1$ before entering the para-ortho-conversion catalyst. After flowing through the para-ortho-conversion catalyst, the hydrogen measuring stream exhibits a temperature $T_2$. The calculation of the para content takes place analogously to that of Example 1.

As mentioned above, the invention also relates to a device according to the invention for performing the process according to the invention.

The apparatus for performing the process according to the invention is characterized by a feedline through which a hydrogen gas stream is fed to a reactor or reaction zone containing a para-ortho-conversion catalyst, the para-ortho-conversion catalyst being thermally insulated relative to the surrounding area, at least one temperature-measuring device arranged at the inlet to the catalyst and at least one temperature-measuring device arranged at the outlet from the catalyst, through which the hydrogen gas stream is removed from the para-ortho-conversion catalyst.

With respect to pressure, to facilitate operation of the device, the pressure at the inlet to the para-ortho-conversion catalyst can be assumed to be the prevalent pressure of the hydrogen in the region from which it is removed, e.g., the pressure in the connecting line between the hydrogen liquefier and the hydrogen storing tank. In addition, the pressure drop within the device is relatively small and can be ignored, so that $p_1$ is equal to $p_2$. Alternatively, pressure measuring devices can be provided at the inlet and/or outlet from the catalyst.

Preferably, the hydrogen gas stream is conveyed through a heat exchanger and cooled therein before being fed to the para-ortho-conversion catalyst.

Figure 2:
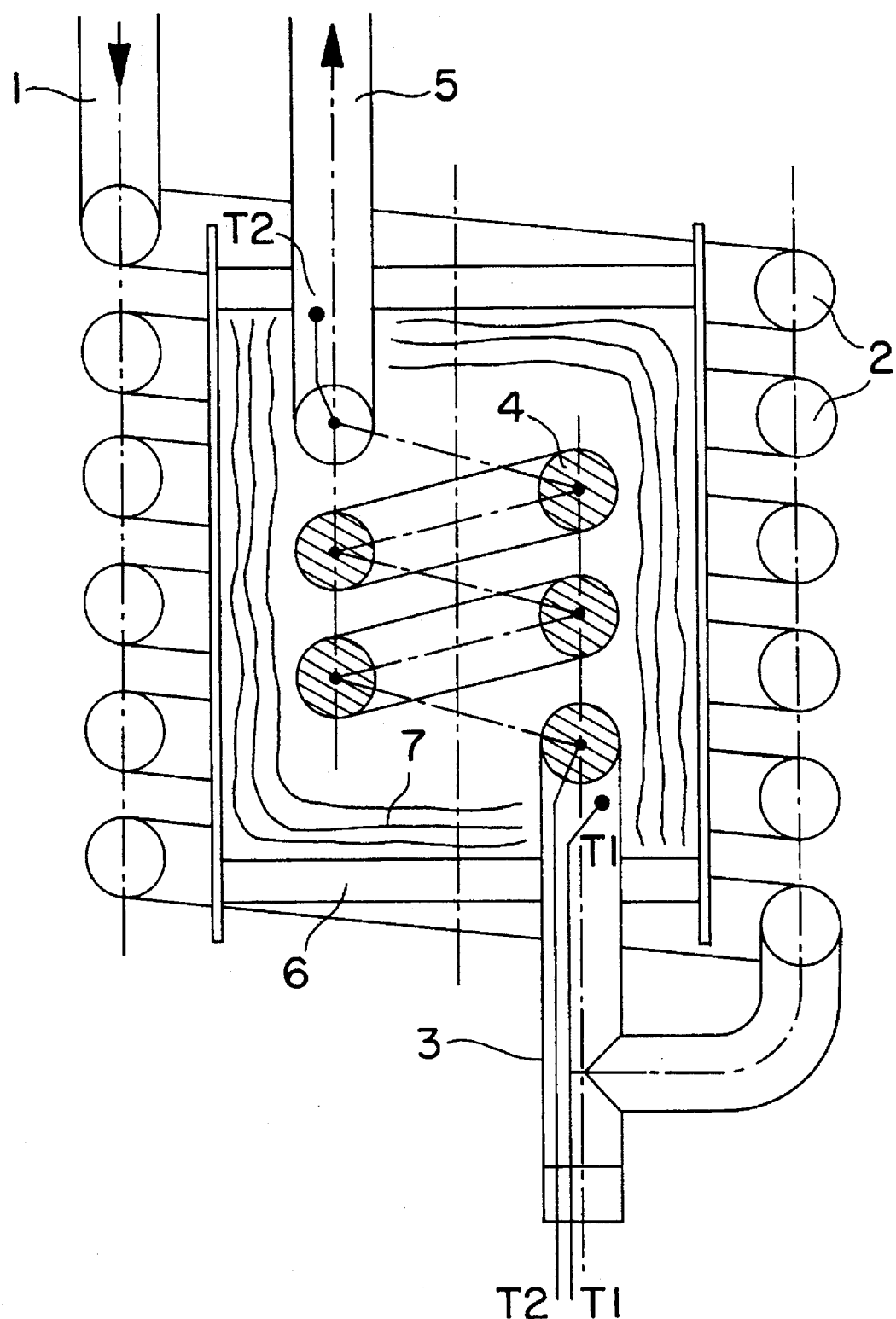
FIGS. 2 and 3 each illustrate embodiments of the device according to the invention for performing the process according to the invention.

FIG. 2 shows one embodiment for a device in accordance with the invention for determining the para content of a hydrogen gas stream. A hydrogen gas stream, with a known pressure, is fed through line 1. This hydrogen gas stream is a measuring stream, e.g., removed from a connecting line between a hydrogen liquefier and a hydrogen storage tank. The device according to the invention represented in FIG. 2 is arranged inside a refrigerant bath, preferably a liquid nitrogen bath. The hydrogen gas stream flows through heat exchanger 2 and is thus heated or cooled by indirect heat exchange to the temperature of the refrigerant used in the refrigerant bath, e.g., 77K in the case of liquid nitrogen. Then, the hydrogen gas stream is fed via connecting line 3 into a reaction zone containing a para-ortho-conversion catalyst 4. In the case of the device according to the invention represented in FIG. 2, para-ortho-conversion catalyst 4 is arranged inside a pipe coil.

Para-ortho-conversion catalyst 4, or the part of the pipe coil that contains the catalyst, is placed inside thermally insulated housing 6. A vacuum preferably prevails inside this housing. Optionally, the insulation is improved even more by so-called superinsulation 7. One temperature- and optionally pressure-measuring device T1 is arranged at the inlet and another, T2, is arranged at the outlet of the catalyst section. A hydrogen gas stream entering the para-ortho-conversion catalyst is converted to the equilibrium concentration, the heat of transition, depending on para-content, leads to cooling or heating of the hydrogen gas stream. This temperature change can be determined from the difference of the temperature measured before and after the para-ortho-conversion catalyst.

Figure 3:
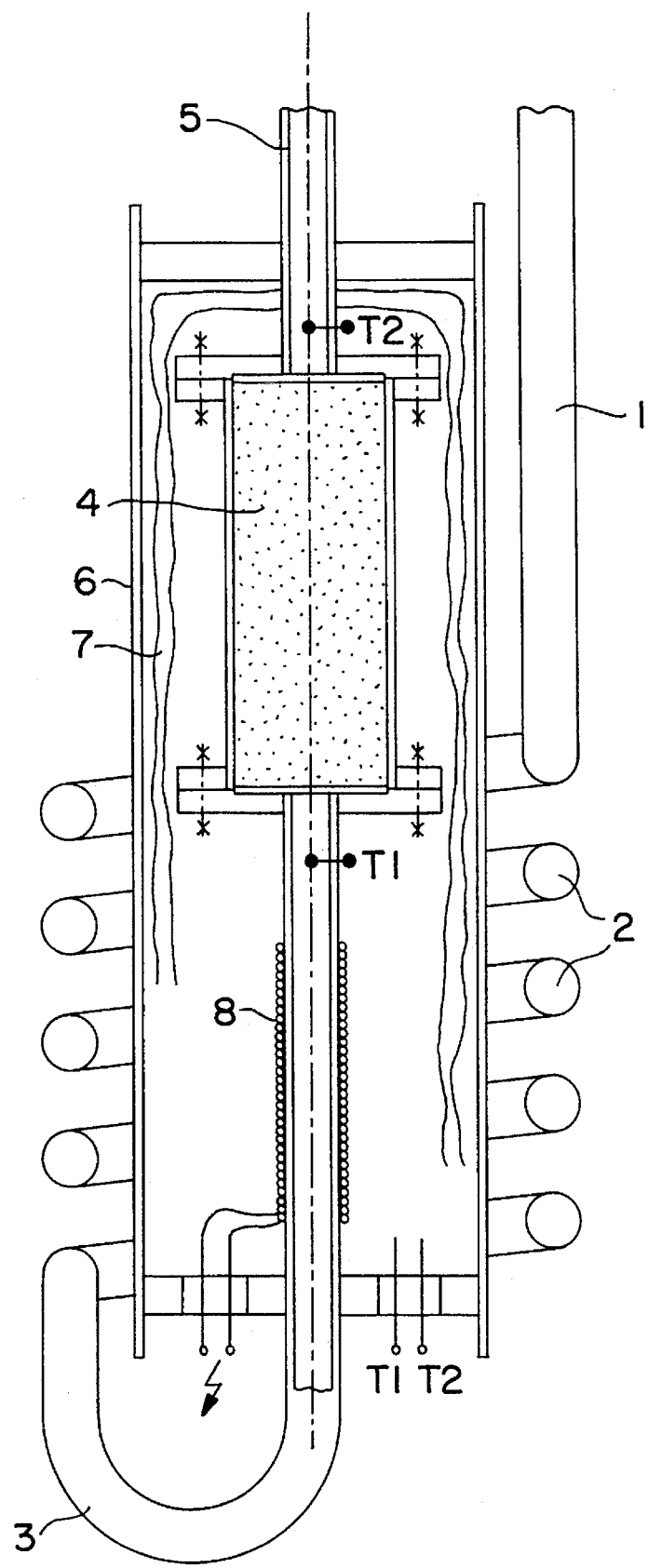
Figure 4:
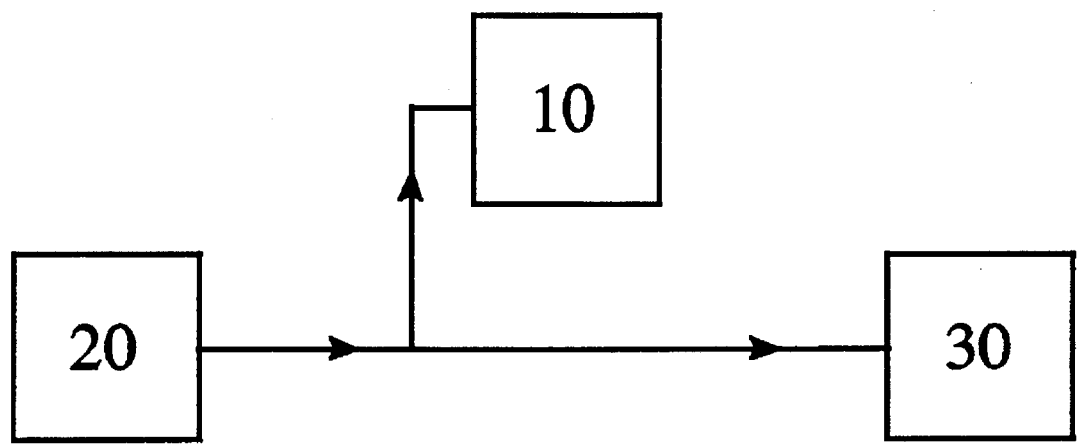
FIG. 4 illustrates an embodiment of a system according to the invention comprising a hydrogen gas liquefier or liquid hydrogen storage tank and a means for determining para hydrogen content.

In the embodiment of the device according to the invention represented in FIG. 3, a hydrogen gas stream is first fed via feed line 1 to heat exchanger 2 and then passes via connecting line 3 to para-ortho-conversion catalyst 4 contained in a reaction zone within housing 6, the reaction zone being surrounded by insulation 7. In turn, the device according to the invention is preferably arranged in a liquid nitrogen bath, so that the hydrogen gas stream is heated or cooled to about 77K by indirect heat exchange in heat exchanger 2. In the embodiment of FIG. 3, before introduction into the reaction zone containing catalyst 4, it is possible via heating device 8, attached externally to line 3, to heat the hydrogen gas stream exactly to a preset temperature.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The preferred specific embodiments are, therefore, to be construed as merely illustrative, and not limitative of the remainder of the disclosure in any way whatsoever.

The entire disclosure of all applications, patents and publications, cited above and below, and of corresponding German application P 44 03 352.4, are hereby incorporated by reference.

What is claimed is:

1. A device for determining the pan content of a hydrogen gas stream comprising:

a reaction zone containing a para to ortho conversion catalyst, an inlet for introducing a hydrogen gas stream into said reaction zone containing said pars to ortho conversion catalyst and an outlet for discharging hydrogen gas from said reaction zone, said para to ortho conversion catalyst being thermally insulated relative to the surrounding area, at least one temperature-measuring means arranged at the inlet of said reaction zone, at least one temperature-measuring means at the outlet of said reaction zone and a means for determining the para content of said hydrogen gas stream from the temperature measured at the inlet and outlet of said reaction zone and standard values of enthalpy and equilibrium of para-hydrogen.

2. A device according to claim 1, wherein said para to ortho conversion catalyst is a metal oxide.

3. A device according to claim 2, wherein said metal oxide is iron oxide.

4. A device according to claim 1, further comprising a heat exchanger for heating or cooling hydrogen gas before being introduced into said reaction zone.

5. A device according to claim 4 wherein said heat exchanger is arranged inside a refrigerant bath.

6. A device according to claim 4, wherein said heat exchanger is arranged inside a nitrogen bath.

7. A device according to claim 4, wherein a heating means is arranged between said heat exchanger and said para to ortho conversion catalyst.

8. A device according to claim 5, wherein a heating means is arranged between said heat exchanger and said para to ortho conversion catalyst.

9. A device according to claim 1, wherein said reaction zone comprises said catalyst positioned within at least one reaction tube.

10. A device according to claim 1, further comprising first pressure measuring means at the inlet to said reaction zone.

11. A device according to claim 1, further comprising first pressure measuring means at the outlet to said reaction zone.

12. A device according to claim 10, further comprising first pressure measuring means at the outlet to said reaction zone.

13. In a system comprising a hydrogen gas liquefier, a liquid hydrogen storage tank, and a line containing said liquefier and said storage tank, the improvement comprising means for removing a measuring stream from said line, and delivering said measuring stream to a means for determining parahydrogen content, wherein said means for determining parahydrogen content is a device according to claim 1.

* * * * *